United States Patent
Taylor et al.

(10) Patent No.: US 6,381,499 B1
(45) Date of Patent: Apr. 30, 2002

(54) METHOD AND APPARATUS FOR USING VAGUS NERVE STIMULATION IN SURGERY

(75) Inventors: Charles S. Taylor, San Francisco, CA (US); Robert G. Matheny, Carmel, IN (US); Dwight P. Morejohn, Davis, CA (US)

(73) Assignee: Cardiothoracic Systems, Inc., Cupertino, CA (US)

( * ) Notice: Subject to any disclaimer, the term of this patent is extended or adjusted under 35 U.S.C. 154(b) by 0 days.

(21) Appl. No.: 09/574,586

(22) Filed: May 17, 2000

Related U.S. Application Data (60) Division of application No. 09/338,303, filed on Jun. 22, 1999, which is a continuation of application No. 08/935,126, filed on Sep. 22, 1997, now Pat. No. 5,913,876, which is a continuation of application No. 08/887,527, filed on Jul. 3, 1997, now abandoned, which is a continuation-in-part of application No. 08/603,411, filed on Feb. 20, 1996, now Pat. No. 5,651,378.

(51) Int. Cl.[7] .............................. A61N 1/32; A61N 1/36
(52) U.S. Cl. ............................................ 607/118; 607/9
(58) Field of Search ................................ 607/118, 9, 63

(56) References Cited

U.S. PATENT DOCUMENTS

| | | | |
|---|---|---|---|
| 4,646,747 A | 3/1987 | Lundback | 128/643 |
| 4,736,749 A | 4/1988 | Lundback | 128/643 |
| 4,991,578 A | 2/1991 | Cohen | 128/419 |
| 5,053,041 A | 10/1991 | Ansari et al. | 606/148 |
| 5,117,822 A | 6/1992 | Laghi | 128/400 |
| 5,304,220 A | 4/1994 | Maginot | 623/1 |
| 5,330,507 A * | 7/1994 | Schwartz | 607/14 |
| 5,458,625 A | 10/1995 | Kendall | 607/46 |
| 5,522,854 A * | 6/1996 | Ideker et al. | 607/6 |
| 5,578,061 A * | 11/1996 | Stroetmann et al. | 607/4 |
| 5,651,378 A | 7/1997 | Matheny et al. | 128/898 |
| 5,690,681 A | 11/1997 | Geddes et al. | |
| 5,700,282 A * | 12/1997 | Zabara | 607/9 |
| 5,755,682 A | 5/1998 | Knudson et al. | |
| 5,913,876 A | 6/1999 | Taylor et al. | 607/2 |
| 6,006,134 A * | 12/1999 | Hill et al. | 607/9 |

FOREIGN PATENT DOCUMENTS

| | | |
|---|---|---|
| WO | WO 94/18880 | 9/1994 |
| WO | WO 95/01757 | 1/1995 |
| WO | WO95/15715 | 6/1995 |
| WO | WO 96/00033 | 1/1996 |

OTHER PUBLICATIONS

Bell, et al., "Inotropic Responses of the Left Ventricle to Changes in Heart Rate in Anesthetized Rabbits," Can J. Physiol Pharmacol, 65:179–184, Dec. 1985.

Benetti, F. J., "Direct Coronary Artery Surgery with Sahenous Vein Bypass Without Either Cardiopulmonary Bypass or Cardiac Arrest," J. Cardiovasc. Surg. 26:217–22, 1985.

(List continued on next page.)

Primary Examiner—Carl H. Layno
(74) Attorney, Agent, or Firm—Alan W. Cannon; Bozicevic, Field & Francis LLP (57) ABSTRACT

A method and apparatus for facilitating coronary surgery on the beating heart wherein the vagus nerve is electrically stimulated to purposely temporarily stop or substantially reduce the beating of the heart under precisely controlled conditions. The apparatus controllably applies electrical stimulus to pre-selected locations along the vagus nerve and to pre-selected nerve branches related to the heart. The apparatus includes several clip and probe configurations for establishing electrical contact with the vagus nerve. Such purposely caused temporary stoppage or substantial reduction of the beating of the heart facilitates procedures such as suturing of an anastomosis which would otherwise be more difficult because of the motion induced by the beating heart.

20 Claims, 8 Drawing Sheets

OTHER PUBLICATIONS

Benetti, F. J., "Use of Thoracoscopy and a Minimal Thoracotomym in Mammary–Coronary Bypass to Left Anterior Descending Artery, Without Extracorpoeal Circulation," J. Cardiovasc. Surg. 36:159–61, Apr. 1995.

DiMarco, J. P. et al., "*Adenosine: Electrophysiologic Effects and Therapeutic Use for Terminating Paroxysmal Supraventricular Tachycardia,*" Therapy and Prevention Arrhythmia, Circulation 68, No. 6, 1254–1263, 1983.

Fanning et al., "Reoperative Coronary Artery Bypass Grafting Without Cardiopulmonary Bypass," Ann. Thorac. Surg.; 55:486–9, Jan. 1993.

Freilich, A., "*Adenosine and Its Cardiovascular Effects,*" American Heart Journal, vol. 123, No. 5, pp. 1324–1328, May 1992.

Klassen et al., "*Coronary Venous Pressure and Flow: Effects of Vagal Stimulation, Aortic Occlusion, and Vasodialators*" Can J. Physiol. Pharmacol. 62:531–538, Oct. 1983.

Th. Lavergne, et al., "Transcatheter Radiofrequency Ablation of Artrial Tissue Using a Suction Catheter," PACE, vol. 12, Jan. 1989, part II, pp. 177–186.

Levy, M., et al., "*Autonomic Control of Cardiac Pacemaker Activity and Atrioventricular Transmission,*" Journal of Applied Physiology, vol. 27, No. 4, Oct. 1969.

Mohiuddin, S. M. et al., "*Safety of Different Dosages of Intravenous Adenosine Used in Conjunction with Diagnostic Myocardial Imaging Techniques,*" Pharmacotherapy 13 (5), pp. 476–480, 1993.

Pfister et al., "*Coronary Artery Bypass Without Cardiopulmonary Bypass,*" Ann. Thorac. Surg.; 54:1085–92, Feb. 1992.

Randall, W. C., "*Parasympathetic Control of the Heart,*" Nervous Control of Cardiovascular Function, Chapter 4, pp. 68–94 (1984).

Stevens, et al., "Closed Chest Coronary Artery Bypass with Cardioplegic Arrest in the Dog," $67^{th}$ Scientific Sessions, 238.

Trapp, et al., "Placement of Coronary Artery Bypass Graft without Pump Oxygenator," Journal of the Society of Thoracic Surgeons and The Southern Thoracic Surgeons Assn. vol. 19, No. 1, Jan. 1975.

Westaby, S., "*Coronary Surgery Without Cardiopulmonary Bypass,*" British Heart Journal; 73–203–205, 1995.

\* cited by examiner

METHOD AND APPARATUS FOR USING VAGUS NERVE STIMULATION IN SURGERY

This application is a divisional of U.S. Ser. No. 09/338,303 filed Jun. 22, 1999, which is a continuation of U.S. Ser. No. 08/887,527 filed Jul. 3, 1997, now abandoned which is a continuation-in-part of U.S. Ser. No. 08/603,411 filed Feb. 20, 1996, now U.S. Pat. No. 5,651,378, which is a continuation of Ser. No. 08/935,126 filed Sep. 22, 1997, now U.S. Pat. No. 5,913,876.

BACKGROUND OF THE INVENTION

Coronary artery bypass graft (CABG) surgery has become a well known and conventional procedure, often referred to as "heart bypass" surgery. Such surgery is performed to relieve a condition in which a partially or fully blocked artery is no longer effective to transport blood to the heart and involves removing a portion of a vein from another part of the body, frequently the saphenous vein, to use as a graft and installing this graft at points which bypass the obstruction to restore normal blood flow to the heart. Common though this procedure has become, it is nevertheless lengthy, traumatic and subject to patient risk. Among the risk factors involved is the use of cardiopulmonary bypass equipment, i.e., the so-called "heart-lung machine," to both pump blood and oxygenate the blood so that the patient's heart may be stopped during the surgery, with its function performed by the cardiopulmonary bypass equipment.

Prior to the present invention, it has been found possible to conduct CABG surgery without stopping the heart, i.e., on a beating heart. In such a beating heart procedure, the function of the heart is maintained and the cardiopulmonary bypass equipment is not needed to replace that function. However, since the heart is beating in such a procedure, the surgeon must cope with the movement of the heart, whether the surgery is a bypass procedure or any other type of coronary surgery. Thus, it would be highly advantageous to perform coronary surgery on a stopped heart, but without causing the patient to endure the lengthy, traumatic and risky procedure involved in supporting the patient on cardiopulmonary bypass equipment. The present invention addresses this problem.

The performance of coronary surgery on the beating heart is described by Benetti et al in "Coronary Revascularization With Arterial Conduits Via a Small Thoracotomy and Assisted by Thoracoscopy, Although Without Cardiopulmonary Bypass", Cor. Buropatum, 4(1):22–24 (1995), which is incorporated herein by reference and by Westaby, "Coronary Surgery Without Cardiopulmonary Bypass" in the March, 1995 issue of the British Heart Journal which is incorporated by reference herein. Additional discussion of this subject matter can be found in Benetti et al, Chest, 100(2) :312–16 (1991), Pfister et al, Ann. Thorac. Surg., 54:1085–92 (1992), and Fanning et al, Ann. Thorac. Surg., 55:486–89 (1993). These articles discuss the further details of grafting by anastomosis of a saphenous vein or mammary artery to diseased coronary arteries including the left anterior descending artery (LAD) or the right coronary artery (RCA), temporary occlusion of the coronary artery to provide a bloodless anastomotic field, use of a double suture placed above and below the point of anastomosis, and use of a running suture for the anastomosis. These articles also contrast the beating heart procedure to the more widely used CABG method performed on the non-beating heart with cardiopulmonary bypass.

SUMMARY OF THE INVENTION

In heart surgery performed while the heart is beating, the surgeon is faced with a moving organ which places increased demands on his skill in performing the desired procedure, e.g., an anastomosis of the left anterior descending artery (LAD) to the internal mammary artery (IMA), or anastomosis of both ends of a free graft means to a target artery and a coronary artery. If, without substantial harm to the patient, the heart could be momentarily substantially stopped or slowed while the surgeon performed the desired task, e.g., taking a stitch or stitches with a suturing needle, such a task would be less difficult to accomplish.

The intentions of the present invention are to provide a surgical procedure in which the heart is momentarily substantially stopped or slowed in a predictable and reliable manner to facilitate the surgery, by electrically stimulating the vagus nerve. This stimulation can be accomplished by first gaining access to the vagus nerve in the chest preferably via the thoracotomy used in the surgery, or in the neck through endoscopic procedures or through a small incision. A suitable electrical stimulating device is then used to briefly apply electric energy to the vagus nerve. For example, separate continuous electrical pulse trains of 10 or less seconds may be intermittently applied to the nerve with, for example, 30 second rest periods between each stimulation. A 50 millihertz current may be used, but the present invention is not limited to any particular quantitative amount of electrical energy. The present invention further provides associated apparatus in the form of various clip or probe means for efficiently electrically coupling the nerve stimulating device or insulated pacing wires to a patient's vagus nerve.

The time of the stimulation and amount of current applied will vary according to the type of surgery and the nature of the task for which the substantial stopping or slowing of the heart is desired. In any event, the normal sinus rhythm of the heart is rapidly restored by natural forces once the stimulation is terminated. Thus, for repetitive tasks such as stitching during suturing, the stimulation may be repeatedly applied for brief intervals during which time the task can be performed under less difficult conditions than would apply if the heart were beating in a normal manner.

For reasons of safety, one or more heart pacing devices, such as a Pace port-Swann pulmonary artery catheter, may be inserted in conventional fashion to the patient's heart and used to restore the beating of the heart during the surgery in the event the heart is slow to revive after a nerve stimulating signal is turned off.

The role of the vagus nerves in the control of cardiac rate and rhythm has been recognized for more than three centuries. Furthermore, soon after electrical stimulating devices became available, it was shown that vagal stimulation caused a reduction in heart rate and, as earlier as 1897, Hunt carried out a quantitative study of the effects of vagal stimulation on heart rate; see, for example, Hunt, R., "Experiments on the Relation of the Inhibitory to the Accelerator Nerves of the Heart", J. Exp. Med. 2:252–279 (1897). An excellent discussion of this phenomenon is found in Chapter 4, Parasympathetic Control of the Heart, by Levy and Martin, in Nervous Control of Cardiovascular Function, edited by Randall, Oxford University Press (1984), which is incorporated by reference herein. However, in spite of the fact that the effect of vagus nerve stimulation on heart rate has long been known, it is believed that this knowledge has not previously been applied to coronary surgery. Rather, vagus nerve stimulation for other purposes has been employed, e.g., as disclosed in the Schwartz U.S. Pat. No. 5,330,507 where vagus nerve stimulation is used in connection with treating arrhythmias, and in the Kendall U.S. Pat. No. 5,458,625 which addresses the use of vagus nerve stimulation for the alleviation of substance withdrawal symptoms or the provision of pain relief, stress relief, and/or general muscle relaxation.

Thus, the present invention is believed to be the first use of vagus nerve stimulation to facilitate coronary surgery, wherein heart motion purposely is stopped or slowed for preselected momentary periods of time during the coronary surgery without need for cardiopulmonary bypass support.

DETAILED DESCRIPTION OF THE INVENTION

The vagus nerve stimulation technique and apparatus of the present invention may be used in open chest coronary surgery where a sternotomy is used to gain access to the heart, or in closed chest, beating heart coronary surgery in which a thoracotomy or a stab wound (puncture) is used to gain access. The following is an exemplary usage of the latter procedure.

The patient is intubated with a double-lumen endobronchial tube which allows selective ventilation or deflation of the right and left lungs. The left lung is deflated to provide access to the heart and the left internal mammary artery (LIMA). The preferred surgical position of the patient is right lateral decubitus, 30° from horizontal, with the left arm above the head.

Surgery begins with a left anterior thoracotomy over the fourth intercostal space. Other sites are suitable depending on the patient's anatomy, particularly the fifth intercostal space. A retractor is used to spread the ribs to provide access to the beating heart. The size of the thoracotomy varies depending on the patient, but generally is less than 12 cm. The parietal pleura is dissected and separated from the ribs, to permit the introduction of a thoracoscope through a trocar at the fourth intercostal space along the medial axillary line. The thoracoascope may be introduced through other areas such as the fifth through seventh intercostal spaces, again depending on the patient's anatomy. The thoracoscope is positioned to provide visualization of the LIMA. The LIMA is then dissected with suitable instruments introduced through the thoracotomy. These instruments generally comprise scissors, clippers, pliers, electrocauteries or other conventional devices useful for the dissection. It is sometimes useful to make a graft with a radial artery coming out from the LIMA in a T-form. This allows formation of anastomosis with multiple coronary arteries such as sequential grafts to the diagonal (Dx) and circumflex (Cx) arteries.

Following dissection of the LIMA, a small pericardial incision is made to expose the LAD. Access to the LAD and Dx arteries is typically relatively easy, requiring an incision of about 5 cm. Access to the Cx artery depends on the patient's characteristics and location of the vessels. In some cases, a graft to the Cx artery requires increased rotation of the patient to the right lateral decubitus and some extension of the pericardial incision. Heparin, or other suitable anticoagulant, may be administered to the patient in an appropriate dose such as 1.5 mg/kg.

At this juncture, an arteriotomy is made in the LAD at a point distal to the obstruction to be bypassed. To prevent excess bleeding and partially stabilize the vessel, a segment of the LAD is occluded with ligating stay sutures comprising 2.5 cm lengths of 5/0 polypropylene or other appropriate ligature material. Vagus nerve stimulation, in accordance with the present invention, may be performed while making the arteriotomy and/or while placing the ligatures to facilitate the surgeon in forming a more precise arteriotomy and/or more accurately placing the ligatures. Applying tension to the ligatures helps stabilize the LAD even though the heart is beating. Other conventional means for occluding and stabilizing the artery may be suitable as well. Furthermore, forceps are also introduced through the thoracotomy to further stabilize and retract the LAD. A scalpel is then introduced to perform an arteriotomy in the LAD. An anastomosis between the LIMA and the LAD is then performed by suturing with 7/0 polypropylene using a needle manipulated by a forceps.

Here again, the vagus nerve stimulation in accordance with the invention is used to temporarily stop or slow the heart to reduce motion in the anastomotic field, such that one or more suturing stitch(es) is/are taken immediately after stimulation when the heart's motion is temporarily stopped or substantially reduced. The number of stitches required may dictate the number of occasions on which electrical stimulation of the vagus nerve will be desirable as well as dictate the duration of the individual electrical stimulations. This in turn, generally requires intermittent electrical stimulation of the nerve, with a selected plurality of seconds, e.g., 30, of rest between stimulations. However, only one electrical stimulation may be necessary throughout the placement of the suturing stitches. It is to be understood that the vagus nerve stimulation in accordance with the invention may be used during other cardiac surgery procedures in which it is desirable to provide a stable surgical site by arresting or substantially slowing the beating of the heart. One such procedure is the procedure for performing the previously mentioned arteriotomy in the LAD or the placement of ligatures around the LAD. The technique and apparatus for applying the stimulating electrical impulses to the vagus nerve in accordance with the invention are discussed below with reference to the various figures.

Upon completion of the anastomosis, the anticoagulant is reversed, if necessary, by suitable means such as the injection of protamine. The hemostasis should be carefully controlled. The thoracotomy is closed by conventional means. If the pleura has not been breached, a small tube for drainage may be left in place and removed the same day as the surgery. If the pleura is open, a larger tube should be left in place for 24 hours. The drainage tube may be introduced through the small incision for the thoracoscope.

In the foregoing procedure, the electric stimulator, e.g., of the type disclosed in the U.S. Pat. No. 5,458,625 may be attached to the patient's ear, neck, or other points of access to the vagus nerve as further disclosed below. The electrodes used to stimulate the vagus nerve may be invasive, e.g., needles or non-invasive clips, examples of which are described below with reference to the figures. The electrical energy supplied to the vagus nerve will vary with the type of equipment used, the point in the body at which access to the vagus nerve is obtained, etc. and it is to be understood that the practice of the present invention is not limited to any particular values. Rather, the appropriate amount of electrical energy needed to achieve the desired result can be readily determined empirically once the type of equipment, point of access, etc. are known. By way of example only, the electrical stimulation applied to the nerve may be derived by a continuous five second train of electrical pulses at 25 Hertz (Hz), 20 volts, with a pulse width of 0.1 millisecond (ma) delivered, for. example, by a Grass Model SD9J Stimulator manufactured by Grass, Inc., W. Warwick, R.I.

FIGS. 1–5 illustrate by way of example only, one embodiment of a vagus nerve clip for detachably attaching the leads of a nerve stimulator device, or similar electrical impulse generating device, to a patient's vagus nerve to momentarily stop or slow the heart in accordance with the present invention. The intent of the invention is to facilitate an otherwise beating heart coronary surgery procedure, without the need for cardiopulmonary bypass support usually required in CABG surgery where the heart is arrested for the entire surgery. The clip is minimally invasive while still providing precise and efficient electrical contact with the vagus nerve. It is to be understood that although a detailed description is made herein relative to the specific clip configuration of FIGS. 1–5, the underlying features illustrated in the FIGS. 1–5 and the attendant functions and advantages thereof, are equally applicable to the clips and probes of other configurations illustrated in part in, and not limited to, FIGS. 5A through 9B and 12–21.

As relates to cardiac function, the right vagus nerve primarily controls the sinoatrial (SA) node, while the left vagus nerve controls the atrioventricular (AV) node of the heart. The AV node seems to be the most effective in arresting the heart in accordance with the invention. As an example of the method of practicing the invention, the heart has been stopped for about 40 seconds at a time by electrical stimulation at, for example, clip position #1 (FIG. 22) allowing for two or three suture bites to be taken. Stimulating the right vagus nerve shuts down the SA node, but breakthrough regulation coming from the AV node at a rate of 50 to 60 beats per minute may make the right vague nerve stimulation less effective in arresting the heart. The heart can be stopped without stimulating all of the parts of the vagus nerve complex that feed to the heart. It follows therefore, that the use of a single clip at a selected clip position, as further discussed with respect to FIG. 22 below, generally is satisfactory to arrest the heart in accordance with the invention. However, more than one clip may be employed at various locations along the vagus nerve.

Figure 1:
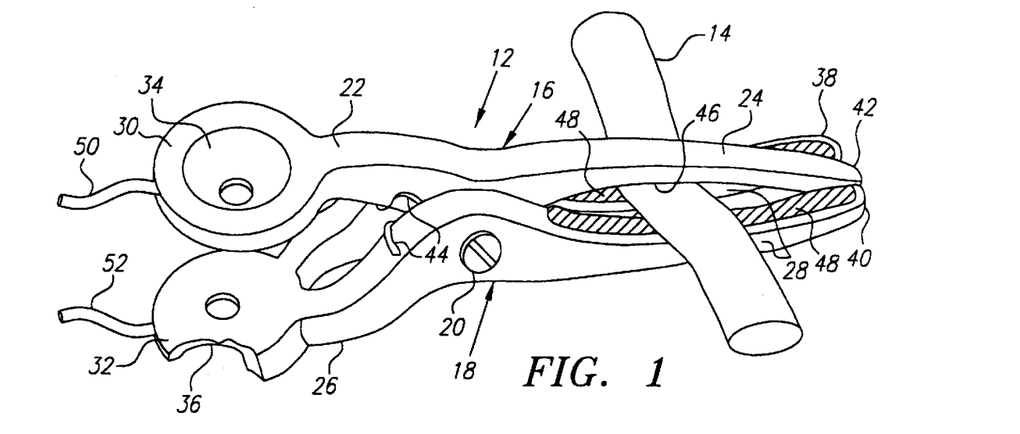
FIG. 1 is a perspective view illustrating, by way of example only, a vagus nerve clip in accordance with the invention.
Figure 2:
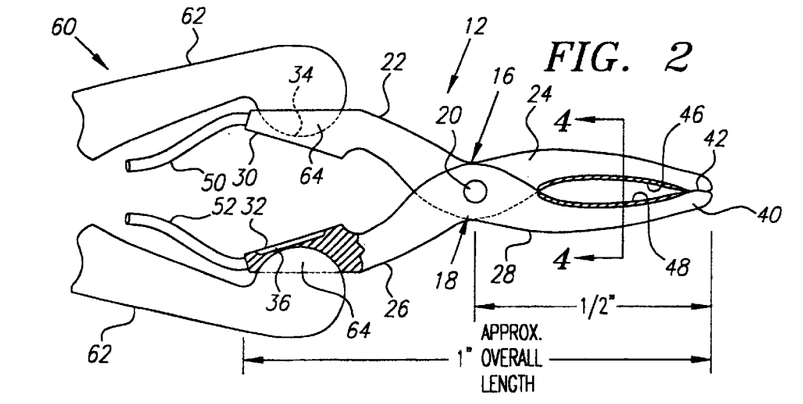
FIG. 2 is a side view of the clip of FIG. 1.

In FIG. 1, an embodiment of a vagus nerve clip 12 is depicted in perspective view properly attached in electrical contact to a preselected portion of a vagus nerve 14. As mentioned supra, various sites or positions for attachment of the clip, or clips, are available along the lengths of the right and/or left vagus nerves, with preferred attachment positions being those which are readily accessible and/or which, when stimulated, sufficiently eliminate the stimulus from the brain to the heart to achieve the desired function and results of the present invention. The various preferred clip attachment positions for achieving the required vagus nerve stimulation will be further discussed below relative to FIG. 22.

Referring to FIGS. 1–4, the clip 12 includes a pair of co-acting members 16, 18 pivotable about a common pin 20. Member 16 includes a handle 22 at one extremity thereof and a grasping jaw 24 at the opposite extremity thereof. Likewise, member 18 includes a handle 26 and a grasping jaw 28 at an opposite extremity thereof. The proximal ends of the handles 22, 26 are provided with relatively large diameter grips 30, 32, respectively, which include respective spherical depressions 34, 36. The large diameters and the associated spherical depressions provide a gripping configuration for receiving the complementary working ends of a suitable clip applicator, such as those further described below in FIGS. 10, 11. In addition, the relatively large diameter handles/depressions allow the clip 12 to be manually grasped by a surgeon for manual placement of the clip on the vagus nerve without using an applicator such as those of FIGS. 10, 11.

The opposing jaws 24, 28 are of selected length sufficient to readily enclose the vagus nerve, which generally has a diameter of from 1/16 to 1/8 inch in the portions thereof where the clip is attached. In a preferred embodiment, the member 18 may be forked in the mid portion or the handle portion to form a pair of parallel members having a pair of jaws which terminate in tips 38, 40. The member 16 fits between the pair of members (18) along the lengths thereof and is pivotally secured relative to the member 18 in the region of the pin 20, and terminates in a tip 42. The jaws may be slightly concavely curved in shape to allow the tip 42 to sufficiently close on the opposing tips 38, 40 while preferably allowing space between the jaw mid-portions to provide a firm attachment of the clip 12 to the nerve 14 regardless of variations in size. See for example, FIG. 2 in particular. The clip 12 is spring loaded closed via, for example, a wire spring 44, FIG. 1. Other spring configurations such as, for example, a flat expanding spring in the region of the handles 22, 26, may be used instead.

In accordance with the invention, the inner confronting surfaces of the jaws 24, 28 are formed to define extended grooves therein along their lengths. The grooves are configured to receive electrically conductive elongated electrodes 46, 48 embedded in the grooves in the confronting surfaces of the jaws 24, 28, respectively. The electrodes 46, 48 are coupled to respective electrical leads 50, 52 which, in turn, are connected to a suitable electrical nerve stimulating device as depicted for example in block diagram in FIG. 22.

Figures 3, 4:
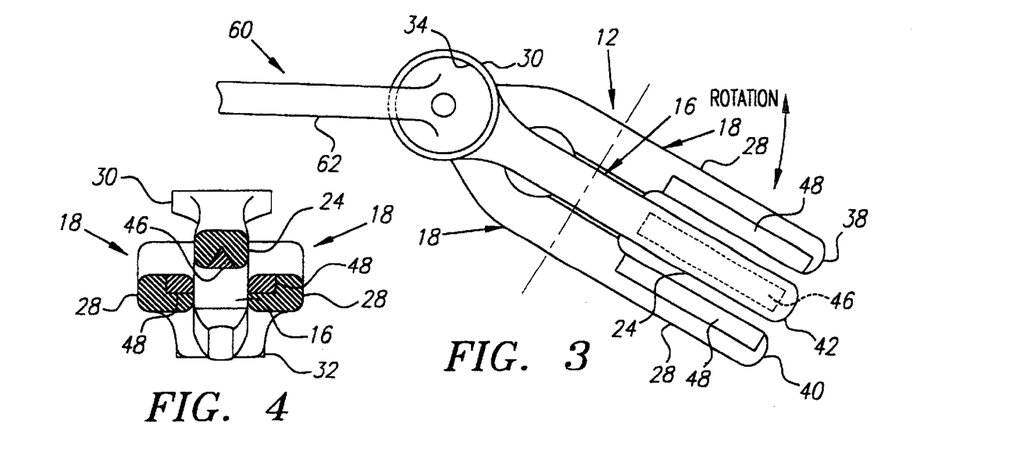
FIG. 3 is a top view of the clip of FIGS. 1 and 2.
FIG. 4 is a cross-sectional end view of the clip of FIGS. 1–3 taken along section line 4—4 of FIG. 2.
Figure 5:
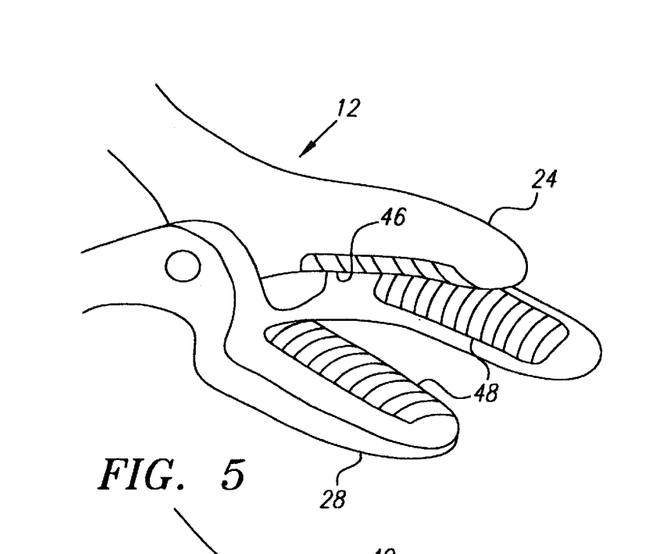
FIGS. 5, 5A, 5B are a partial perspective and two cross-sectional views, respectively, of the clip of FIGS. 1–4 depicting different electrode cross-sections.

As depicted in FIGS. 5–9, the electrode 46 may be at a positive potential and the electrodes 48 may be at a negative potential, or vice versa. The configuration of the specific electrodes 46, 48 embedded in the jaws 24, 28 readily is seen in FIGS. 4 and 5. However, many other electrode and jaw combinations are contemplated by the invention, as further illustrated in FIGS. 6–9, 12 and 18–21.

As illustrated in particular in the clip configuration of FIGS. 1, 5 and 5A, 5B, the laterally spaced jaws 24, 29 and integrally embedded electrodes 46, 48 provide a slight yet firm shearing action-when the clip 12 is attached to the vagus nerve 14. In all embodiments, the strength of the spring 44 is selected to provide sufficient force between the electrodes and the nerve to cause the electrodes to bite gently into the nerve to provide positive electrical contact therewith as well as to prevent the clip from falling off the nerve. Since it is important that electrical contact and electrical stimulation be made only with the vagus nerve and not the surrounding vessels, tissues, etc., the members 16, 18 of the clip 12 are formed of an electrically non-conductive material such as, for example, a plastic material. Thus, as evident in FIGS. 4, 5, 5A, 5B, et seq., the non-conductive material sufficiently encloses the electrodes of all the configurations to shield them from the surrounding tissues and vessels, while exposing their confronting edges and surfaces for positive contact with the vagus nerve when attached thereto.

Figure 5A:
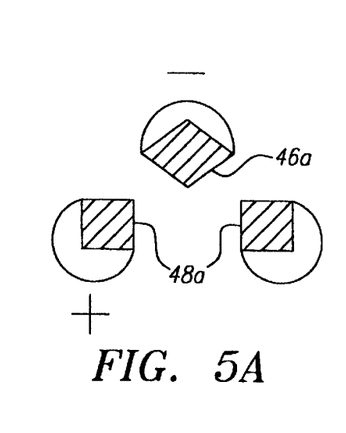
Figure 5B:
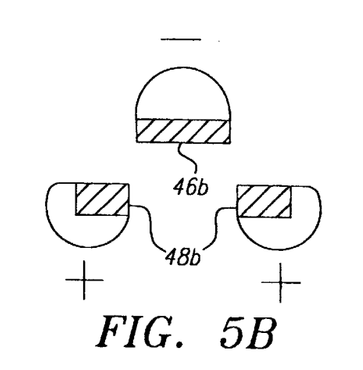

Although the electrodes depicted in FIGS. 4, 5 have arcuate confronting surfaces, other surface and cross-sectional configurations such as square, rectangular, etc., may be employed if desired, for example, to enhance the shearing action and thus the electrical contact and grip of the clip 12 on the nerve 14. For example, FIG. 5A depicts electrodes 46a, 48a with square cross-sections with edges thereof facing each other to enhance their electrical contact with the vagus nerve. Likewise, in FIG. 5B the electrodes 46b and 48b have rectangular and L shaped cross-sections with edges thereof confronting the vagus nerve to enhance the shearing action and contact. In addition, the FIGS. 5A, 5B depict the electrodes 46a, 46b at a negative potential with the electrodes 48a, 48b at a positive potential. However, the potentials may be switched.

Figure 6:
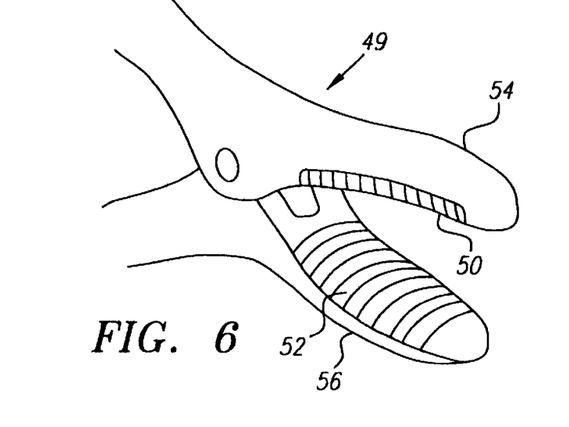
FIGS. 6, 6A, 6B are a partial perspective and two cross-sectional views, respectively, of an alternate clip configuration of the invention.
Figure 6A:
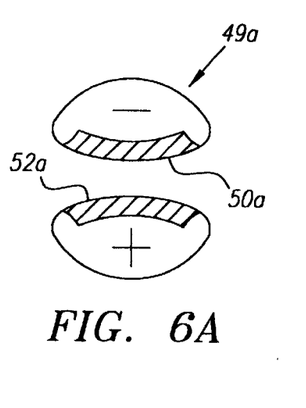
Figure 6B:
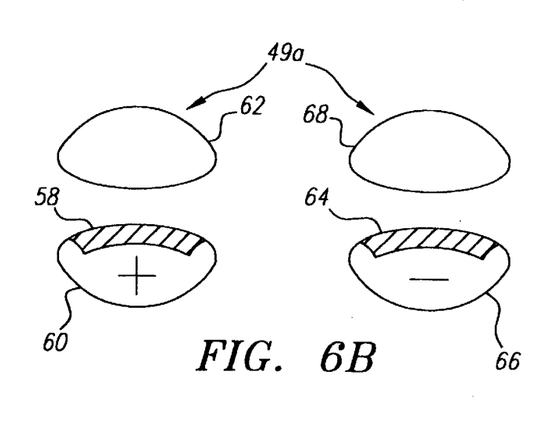

In addition, although FIGS. 1–5, 5A, 5B depict a clip configuration with one jaw/electrode opposing a pair of jaws/electrodes laterally spaced apart, other jaw/electrode numbers and opposing configurations are contemplated by the present invention. For example, a single positive and single negative jaw/electrode combination may be used in a clip 49 as illustrated in FIGS. 6, 6A, wherein electrodes 50, 52 and respective jaws 54, 56 in FIG. 6, and electrodes 50A, 52A in FIG. 6A, are in opposing register with each other so as to press together to provide attachment to and electrical contact with the vagus nerve 14. In FIG. 6B, an electrode 58 of a clip 49b is embedded into the confronting surface of a jaw 60 while a confronting jaw 62 does not include an electrode. However, in a bipolar electrical configuration, a second similar clip 49b may be provided which includes an electrode 64 in a jaw 66 with no electrode in a confronting jaw 68. The clips 49b are spaced apart a selected distance, 1, such as, for example, about 1 to about 2 centimeters (cm) on the vagus nerve, preferably with the proximal electrode at negative potential and the distal electrode at positive potential on the nerve. The selected distance between clips 49b may, however, be less than 1 cm or greater than 2 cm. In FIGS. 6, 6A, 6B the electrodes have an arcuate cross-section.

Figure 7:
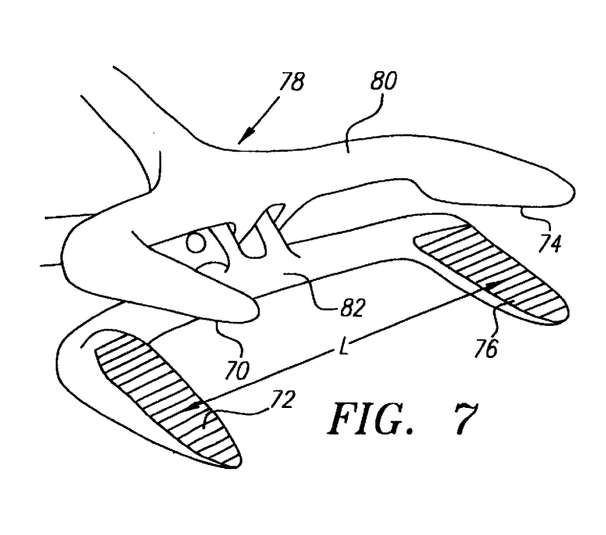
FIGS. 7, 7A, 7B are a partial perspective and two cross-sectional views, respectively, of another clip configuration of the invention.
Figure 7A:
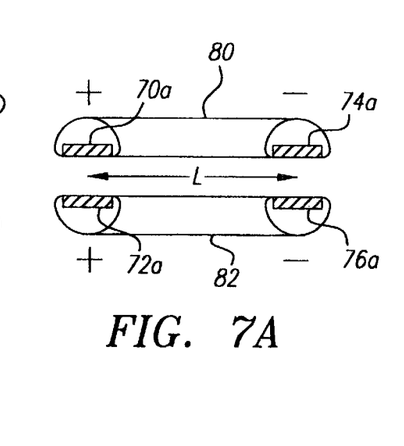

Alternatively, as depicted in FIGS. 7, 7A, two positive electrodes 70, 72 are in confronting relation with two negative electrodes 74, 76 confronting and spaced a distance, 1, from the electrodes 70, 72 to form a clip 78. The electrodes are depicted as generally flat in cross-section and embedded in respective jaws formed of confronting forked members 80, 82 integral with handles, and where the jaws/handles are pivotable relative to each other in a normally closed spring loaded condition.

Figure 7B:
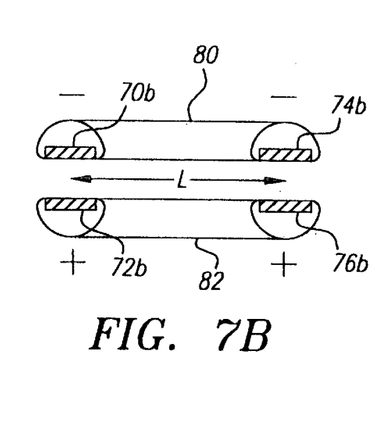

The clip illustrated in FIG. 7B is similar to the clip shown in FIGS. 7, 7A except that the upper electrodes 70b, 74b are of negative potential, with the lower electrodes 72b, 76b being of positive potential. Here also, as in the other clips and/or probe embodiments, the potentials may be reversed.

Figure 8:
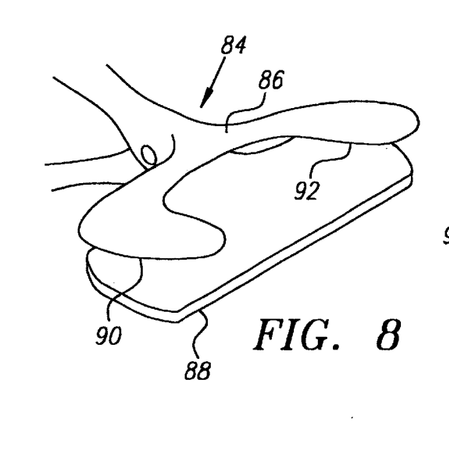
FIGS. 8, 8A, 8B are a partial perspective and two cross-sectional views, respectively, of still another clip configuration of the invention.
Figure 8A:
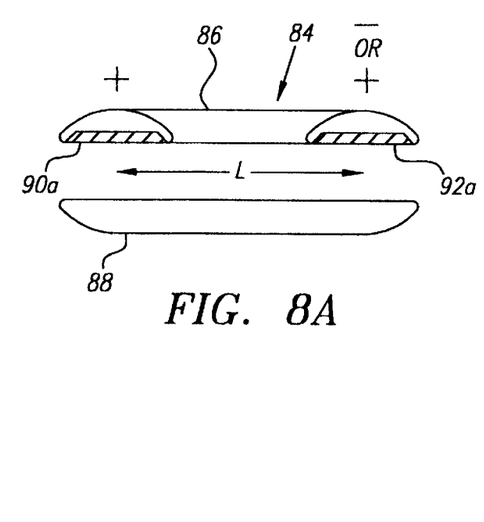
Figure 8B:
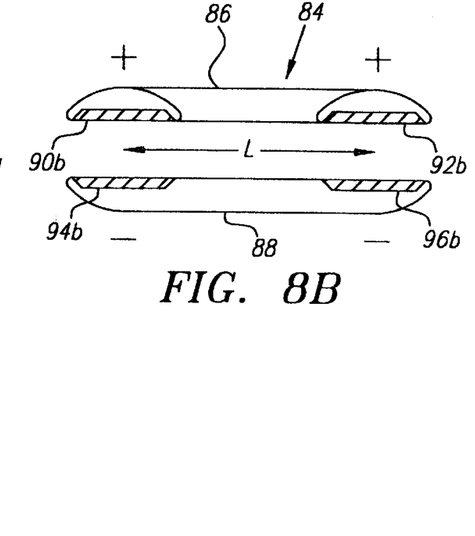

FIG. 8 illustrates another clip configuration 84 wherein confronting jaws are formed of a forked member 86 facing a paddle member 88 in spring loaded normally closed condition. As illustrated in FIGS. 8A, 8B, electrodes may be selectively arranged within the forked and paddle members. In FIG. 8A, a positive and a negative electrode 90a, 92a, are embedded in the jaws of the forked member 86 with no electrode in the paddle member 88. Alternatively, both the electrodes 90a, 92a may be positive (or negative), whereupon a second clip 84 of negative (or positive) electrodes is attached to the vagus nerve in spaced relation to the first clip 84. In a further configuration, positive electrodes 90b, 92b may be provided in the jaws of the forked member 86 with confronting negative electrodes 94b, 96b being provided in the paddle member 88. As in FIGS. 6B, 7A, 7B, the electrodes may be spaced apart a selected distance, 1.

Figures 9, 9A, 9B, 10, 11:
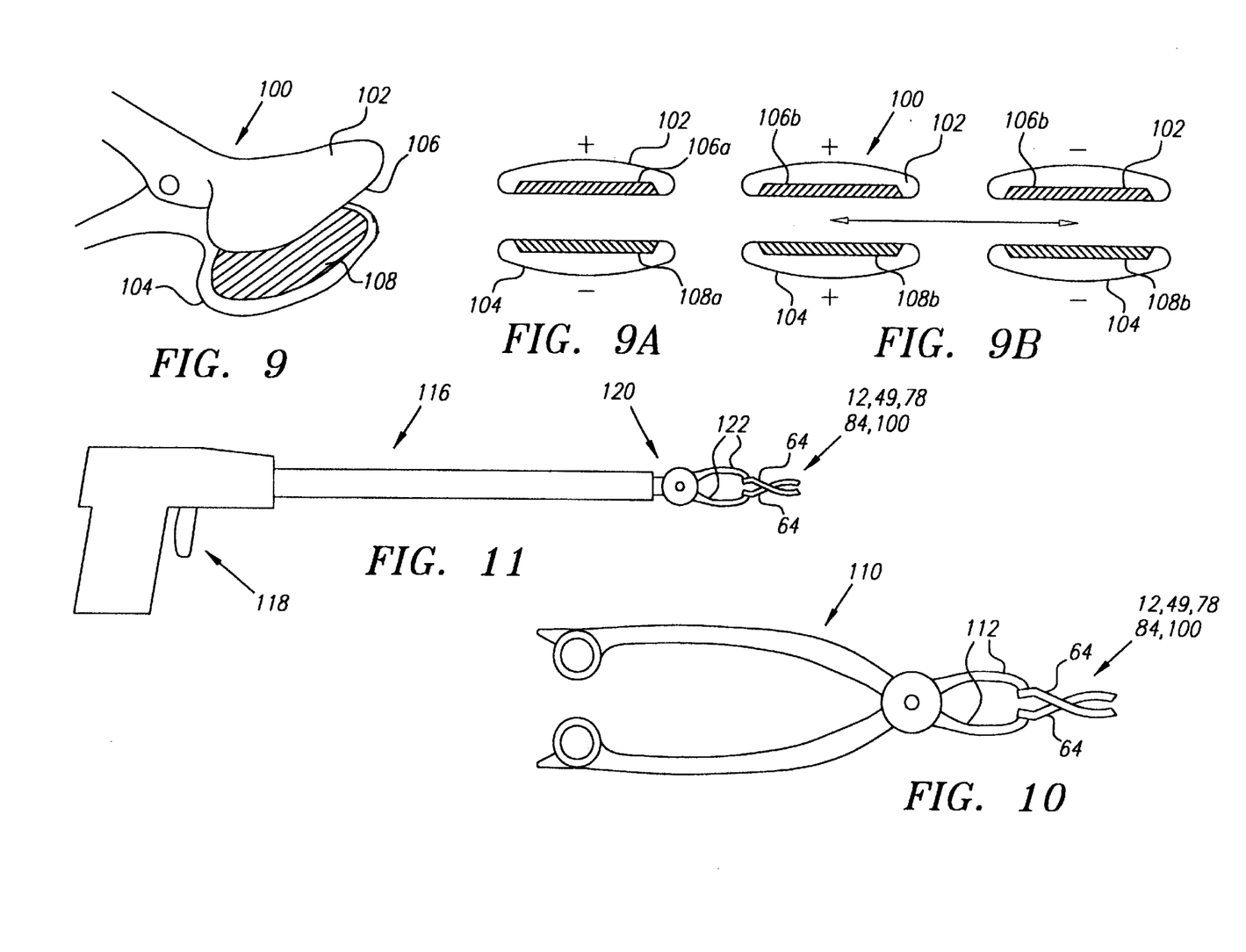
FIGS. 9, 9A, 9B are a partial perspective and two cross-sectional views, respectively, of yet another clip configuration of the invention.
FIG. 10 is a side view illustrating an applicator means for attaching a clip such as the clips of FIGS. 1–9 to the vagus nerve.
FIG. 11 is a side view illustrating another applicator means employed in microsurgical procedures for attaching the clip to the vagus nerve.

FIGS. 9, 9A, 9B illustrate still another clip configuration 100 wherein confronting jaws are formed of two confronting paddle members 102, 104, within which may be embedded relatively large flat positive and negative electrodes 106, 108 respectively, as illustrated in FIG. 9A. Alternatively, a pair of clips 100 may be employed wherein electrodes 106b, 108b of a first clip are both of positive (or negative) potential with the electrodes 106b, 108b of a second clip being of negative (or positive) potential. The clips may be spaced apart a selected distance, 1, and generally are employed when supplying the stimulating signal to the region of the plexus itself as illustrated herein, for example, at position #4 in FIG. 22 below.

FIGS. 10 and 11 depict surgical instruments for holding and attaching respectively modified vagus nerve clips of the invention. To this end, FIG. 10 depicts a pair of surgical pliers 110 modified to allow jaws 112 thereof to firmly engage and hold a vagus nerve clip such as the clip illustrated in FIG. 1. For example, as more clearly shown in FIGS. 2, 3 the distal ends of the jaws 112 of the pliers 110 depicted in FIG. 10, terminate in the semi-spherical ball tips 64, the diameters of which match the diameters of the spherical depressions 34, 36 formed in the handles 30, 32 of the clip 12. See for example FIGS. 2, 3 above, as well as FIGS. 12, 13 below. The relatively large diameter handles 30, 32 and the correspondingly large spherical depressions 34, 36 and snugly fitting spherical ball tips 64, provide a relatively rigid combined holding structure between the pliers 110 and the clips of FIGS. 1–9, to enable a surgeon to precisely control the clip when attaching it to a selected position on the vagus nerve amongst the surrounding tissue and vessels. The spherical configuration also allows the surgeon to rotate the clip relative to the pliers 110 at selected and advantageous offset placement angles, as depicted in FIG. 3. The relatively large spherical configuration also helps in maintaining the selected placement angle of the clip during the procedure of attaching the clip to the nerve. In an alternative configuration, the handles 30, 32 may include the semi-spherical ball 64 and the spherical depressions 34, 36 may be formed in the ends of the applicator jaws 112, such as depicted, for example, in FIG. 13 below.

FIG. 11 illustrates an alternative means for attaching a clip such as those of FIGS. 1–9 to a selected position on a vagus nerve 14, when employing endoscopic surgery procedures using microsurgical instruments. To this end, an endoscopic instrument or applicator 116 includes a usual handle and trigger mechanisms 118 for controlling a distal working end 120 of the applicator 116. The working end of this applicator includes a cooperating pair of jaws 122 operable in response to movement of the trigger mechanism to engage and thus firmly hold a clip in a manner similar to that described with reference to FIGS. 10, 2, 3 and 12, 13. Thus, the jaws 122 and ball-tips 64 of the applicator 116 are of a configuration similar to the jaws 112 and ball-tips 64 of the pliers 110 of FIGS. 10, 2, 3 and those of FIGS. 12, 13, and provide the same functions and advantages. The clips employed in microsurgical procedures however preferably are scaled down in size to allow their passage through associated trocars, etc., commonly used in such microsurgical procedures.

Figure 12:
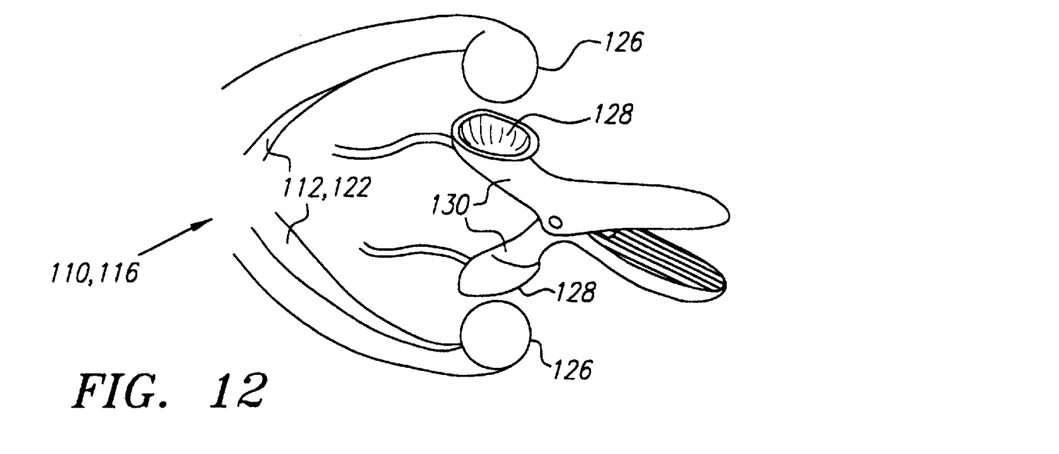
FIGS. 12–14 are partial perspective views of embodiments and modifications of clips and applicator means in accordance with the invention.
Figure 13:
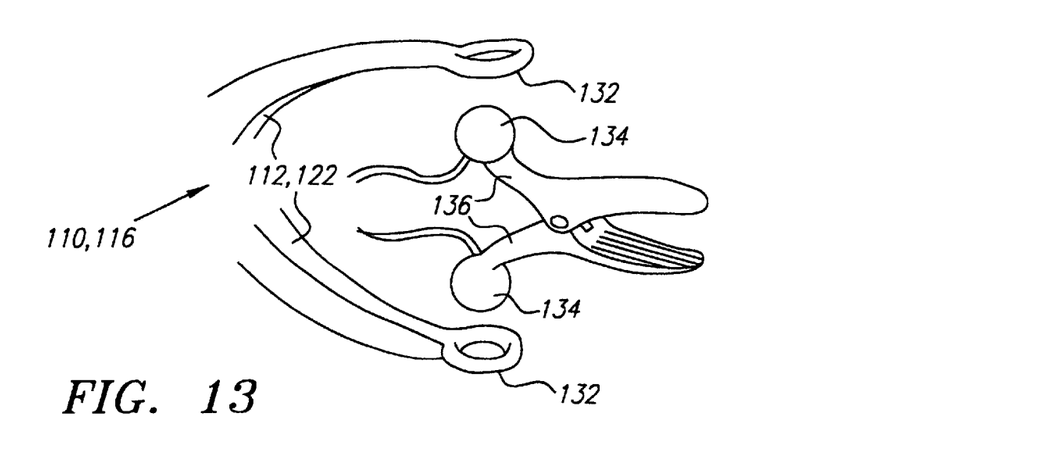

FIGS. 12 and 13 illustrate alternative combined holding structures disposed between the jaws of an applicator such as the applicators 110, 116 of FIGS. 10, 11, and the respective handles of the clips of FIGS. 1–9. Thus, in FIG. 12, the jaws 112 or 122 of the applicator 110 or 116 terminate in ball tips 126 similar to the ball tips 64 of FIGS. 2, 3. Spherical depressions 128 formed in handles 130 of, for example, a clip 49 (FIG. 6) are sized to fit snugly with the ball tips 126.

In FIG. 13, the configurations of the applicator's jaws and of the clip's handles are interchanged such that spherical depressions 132 are formed in the tips of the applicator jaws 112, 122 while ball tips 134 are formed on handles 136 of the respective clip.

Figure 14:
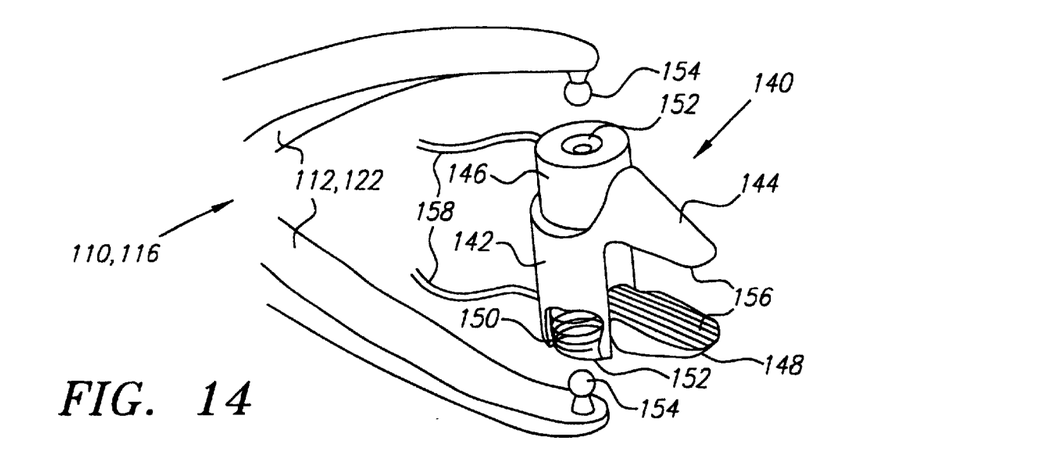

FIG. 14 illustrates an alternative clip geometry for forming a compressible barrel clip 140, and an example of the jaws of a cooperating applicator for attaching the clip 140 to a vagus nerve. To this end, a sleeve 142 is provided with an integral laterally protruding jaw 144. A second member 146 is slidably fitted within the sleeve 142 and is provided with an integral laterally protruding jaw 148 which confronts the jaw 144. A spring 150 is disposed between end portions of the sleeve 142 and member 146 to provide the clip 140 with a normally closed action. The bottom of the sleeve 142 and top of the member 146 are provided with spherical depressions 152 which are adapted to receive respective ball tips 154 formed on the tips of jaws 112, 122 of an applicator 110, 116. Electrodes 156 are embedded in respective jaws 144, 148, as previously described in the previous figures, and are coupled to a nerve stimulating device via leads 158.

FIGS. 15–21 illustrate additional embodiments of means for attaching electrodes to the vagus nerve to allow stimulation thereof to arrest or slow the heart during beating heart surgical procedures. The embodiments of FIGS. 15–21 are depicted adapted for endoscopic surgery procedures wherein attachment of electrodes to the nerve is provided via clip means similar to those of FIGS. 1–13 or via various probe (needle) attachment means.

Figure 15:
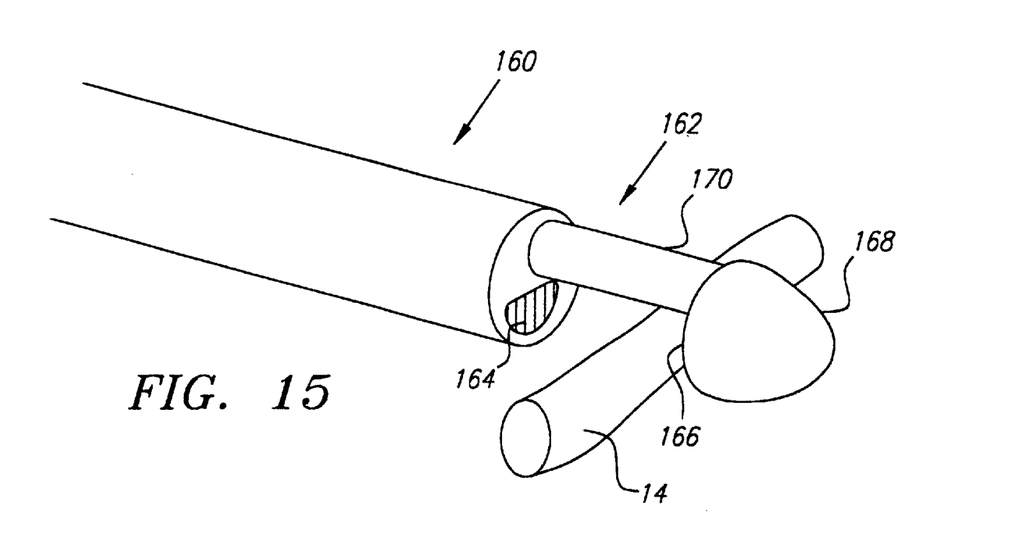
FIGS. 15–21 are partial perspective views of still further embodiments and modifications of clips, probes and applicator means of the invention for endoscopic surgery applications.

FIG. 15 illustrates a distal end of a microsurgical instrument 160 for use in endoscopic procedures, where the distal end includes a clip means 162 formed of a first electrode 164 embedded in a face on the end of the instrument. A second confronting electrode 166 is formed in a translatable cone-shaped cap 168, which cap is axially moveable relative to the electrode 164 via a member 170 translatable within a lumen in the instrument 160. In operation, the instrument is inserted into the chest cavity through the thoracotomy or through a trocar, or into the neck via an incision, and the cone-shaped cap 168 is urged through surrounding tissue, etc., past a desired position on the vagus nerve. The cap 168 and electrode 166 then are translated towards the electrode 164 via the member 170 to capture the vagus nerve 14 between the electrodes.

Figure 16:
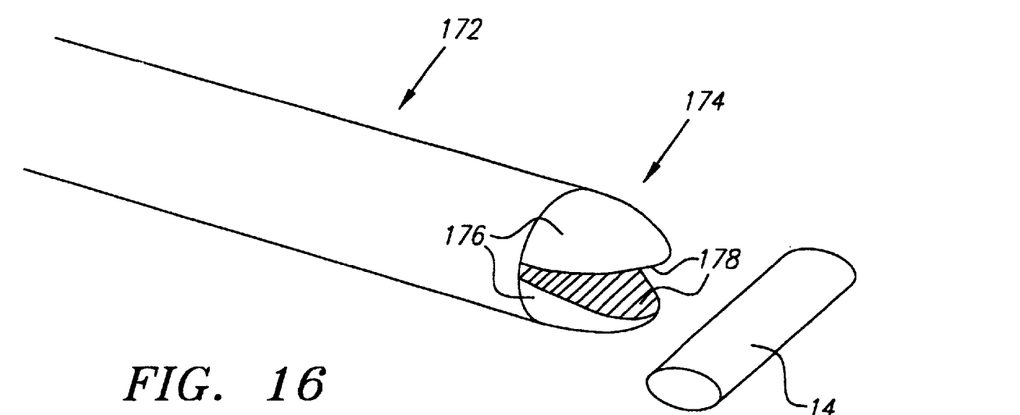

FIG. 16 illustrates the distal end of an endoscopic microsurgical instrument 172 where the distal end includes a clip means 174 formed of confronting jaws 176, each having an electrode 178 embedded in the confronting surfaces of the jaws. The jaws 175 are attached to a translatable member (not shown) within the instrument 172 and are tapered along their outside surfaces, such that partial withdrawal of the jaws 176 into the instrument causes the jaws and thus the electrodes 178 to close about the vagus nerve 14, and vice versa.

Figure 17:
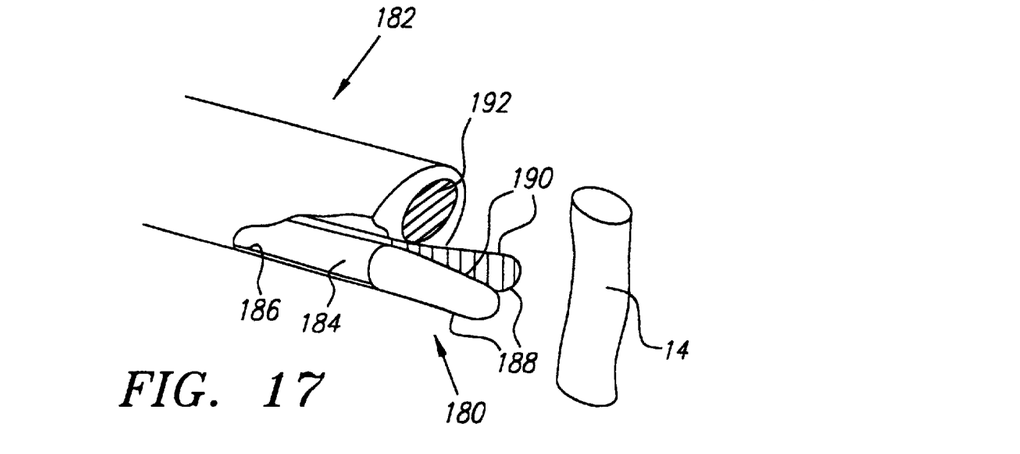

FIG. 17 illustrates a microsurgical instrument 182 with a clip means 180 secured to an end of a translatable member 184 within a lumen 186 in the instrument. The clip means 180 include confronting pivotable jaws 188 containing respective electrodes 190. As in FIG. 16, movement of the jaws 188 from and into the lumen 186 via translation of the member 184 respectively opens and closes the jaws to enable attachment of the electrodes 190 to the vagus nerve 14. Alternatively, jaws 188 may be pivotally hinged at the distal end of member 184, and opened and closed by a push rod or cable type mechanism (not shown) operatively disposed within member 184. To facilitate the attachment process, the instrument 182 may include an endoscope 192 disposed to provide a view of the clip means 180 and of the vagus nerve.

Figure 18:
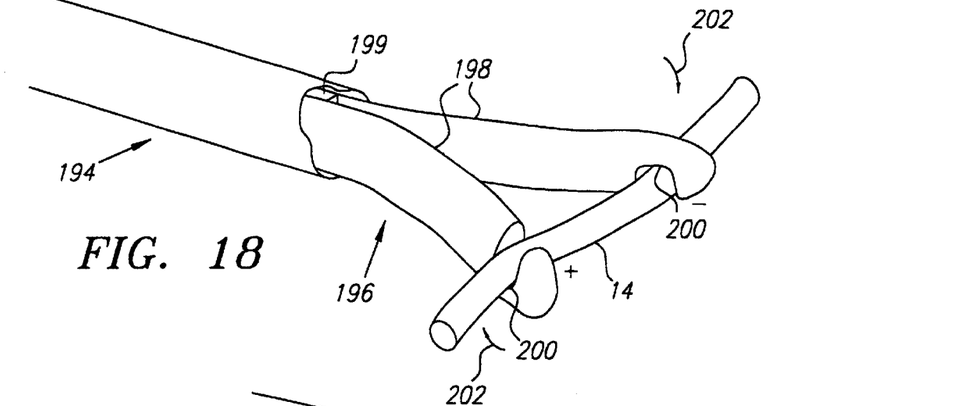

FIG. 18 illustrates still another embodiment of a microsurgical instrument 194 with a clip means 196 formed of a pair of outwardly-biased, spring-like hook members 198 having a semi-cylindrical cross-section. The spring-like hook members 198 may be made of electrically conductive material, with an insulation layer 199 between them in the instrument which also is formed of non-conductive material. When the hook members 198 are pushed from the instrument 194 they diverge to thus spread apart at their ends. The ends are formed with oppositely facing notches 200 whereby the vagus nerve 14 can be captured and then held in electrical contact with a slight rotation of the instrument 194 as depicted by arrows 202. The hook members 198 are at positive and negative polarities, respectively.

Figure 19:
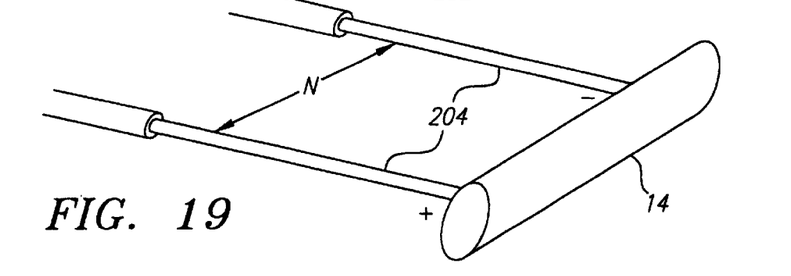

FIG. 19 illustrates an alternative embodiment of means for electrically attaching a nerve stimulating device (FIG. 22) to the vagus nerve to achieve the intent of the present invention. To this end, a pair of needles or probes 204 of positive and negative electrical potential are carefully inserted in the vagus nerve 14 at a selected spaced apart distance, 1, equivalent for example to the distance, l, of previous mention.

Figures 20, 21:
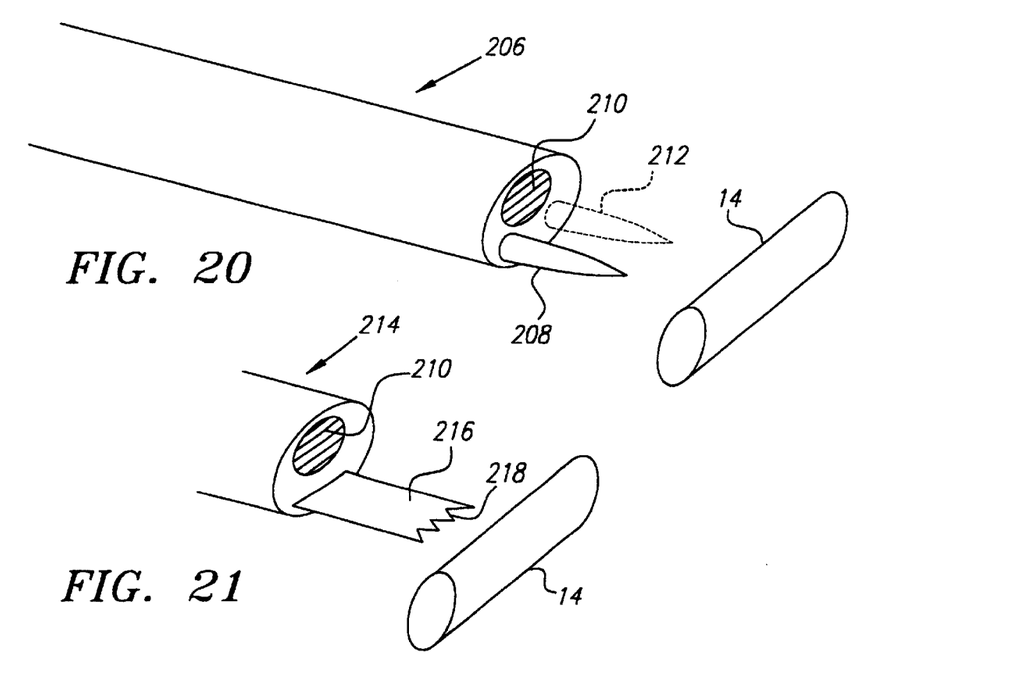

FIG. 20 illustrates another embodiment of a microsurgical instrument 206 with a nerve attachment needle or probe 208 slidably disposed within a lumen in the instrument. The instrument 206 includes an endoscope 210 for providing a view of the probe 208 and the vagus nerve 14. The instrument can be modified to include a pair of probes or needles, one at a positive potential and one at a negative potential, as depicted partially in phantom line at 212. If a single probe 208 is used, a pair of such instruments 206 may be used to provide the positive and negative potentials at a selected spaced distance, n, along the vagus nerve 14.

A modification 214 of the instrument 206 of FIG. 20 is depicted in FIG. 21, wherein the instrument 214 includes a translatable electrically conductive member 216 terminating in a jagged or serrated probe 218 which is capable of making good electrical contact with the vague nerve 14. As mentioned in FIG. 20, a pair of the instruments 214, spaced at a selected distance, may be used. Alternatively, the member 216 may be split lengthwise into two members insulated from each other and defining probes of positive and negative polarity, respectively.

Although the various embodiments of previous description employ a bipolar application of electrical stimulus to the vagus nerve, it is to be understood that unipolar application of electrical stimulus, though of lesser efficiency, may be employed using a single electrode and clip or probe.

Figure 22:
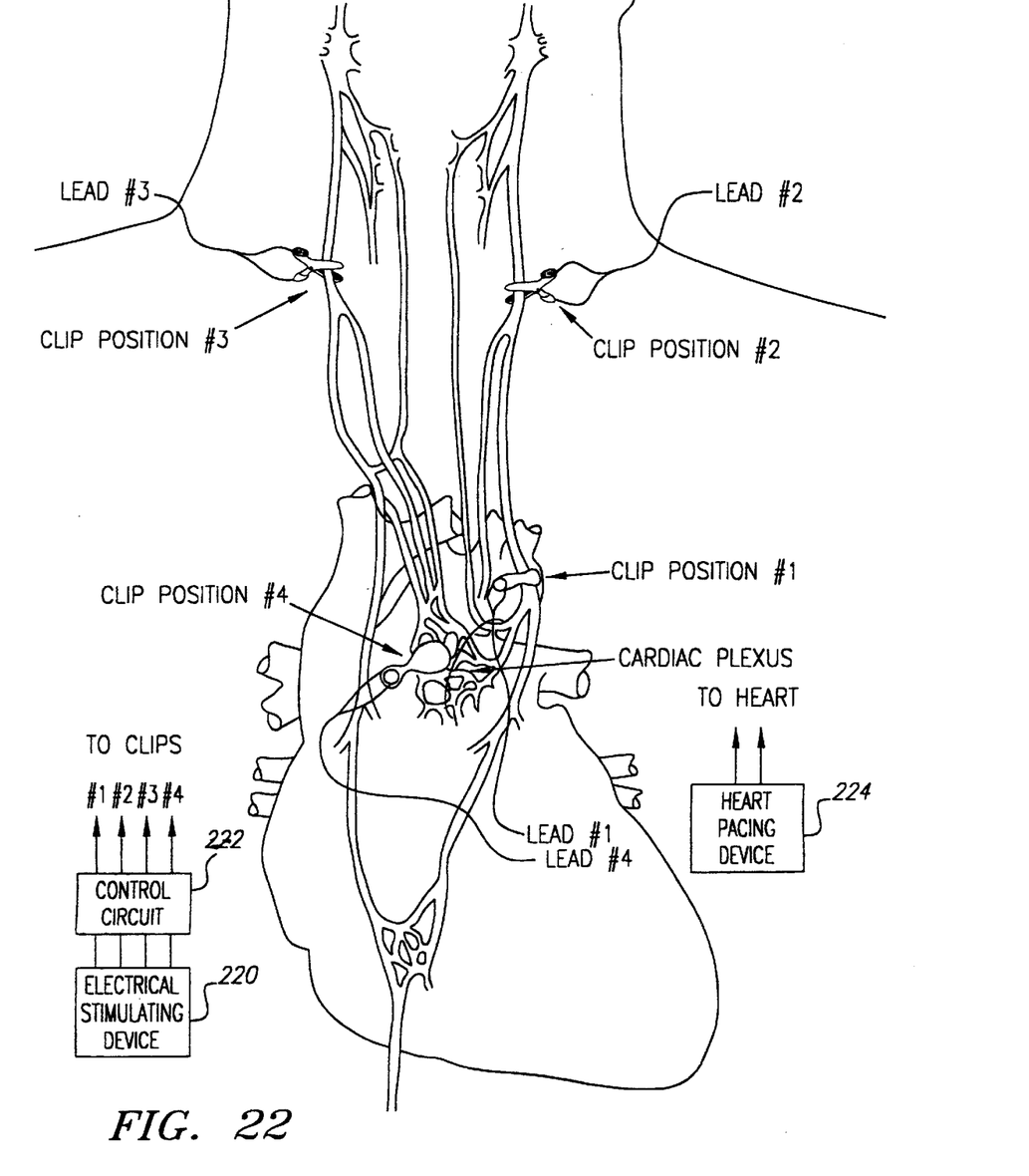
FIG. 22 is a simplified view of pertinent internal portions of a patient's neck and chest, illustrating in particular positions along the vagus nerve where the clip, or clips, may be attached to effect the intended function of the invention.

Referring now to FIG. 22, there is depicted a simplified view of a vagus nerve structure and heart, and of various possible positions on the vagus nerve where the clip means of the present invention may be attached to favorably affect a corresponding nerve plexus in the heart region and, in turn, cause the precisely controlled momentary stoppage or slowing of the heart in accordance with the present invention. To this end, there follows with respect to FIG. 22 a brief explanation of several preferred positions for attachment of a vagus nerve clip such as the vagus nerve clips of FIGS. 1–21, and of the resulting pertinent innervation; that is, the nerves related to the heart that are stimulated by the controlled application of electrical impulses to the clip in that specific position.

Referring to FIG. 22, clip position #1 is on left vagus nerve as it crosses the transverse aorta, just proximal (superior) to the left recurrent nerve branch. The left recurrent nerve gives rise to the inferior thoracic or cardiac nerve branch which terminates in the deep cardiac plexus.

Clip position #2 is on the cervical portion of the left vagus nerve, just proximal to the lower branch of the left superior cervical cardiac nerve. The left superior cervical cardiac nerve, lower branch, terminates in the superficial cardiac plexus. Clip position #2, being proximal to clip position #1, would effect it's innervation as well.

Clip position #3 is on the cervical portion of the right vagus nerve, just proximal to the lower branch of the right superior cervical cardiac nerve. The right superior cervical cardiac nerve, lower branch, terminates in the deep cardiac plexus, the right recurrent nerve which gives rise to one of the (normally) three right inferior thoracic or cardiac branches that terminate in the deep cardiac plexus, and from below the recurrent nerve, the right vagus nerve gives rise to the other (normally) two right inferior thoracic or cardiac branches.

Clip position #4 is on the deep cardiac plexus itself, or branches arising from near the posterior pulmonary plexus that innervate the SA node area. The deep and superficial areas of the cardiac plexus are effective terminals of the cardiac portions of the vagus nerve. The deep cardiac plexus also receives nerve branches from both sides of the vagus nerve above clips #1 and 2, most apparently the right and left upper branches of the superior cervical cardiac nerves. In this position, the preferred attachment means is the paddle clip of, for example, FIG. 8 or 9.

The different clip positions shown in FIG. 22 are accessible through various access openings in the cervical or thorax regions using the applicators 110 or 116 of FIG. 10 or 11. For example, the clip positions #1 through #4 may be accessible via the thoracotomy through which the surgery is being performed, or endoscopically through a percutaneous port, using either the microsurgical applicators 110 or 116. Alternatively, the clip position #1 can be accessed from the left thoracotomy, and can be fairly easily seen using a surgical hook or with a scope. Clip position #2 and #3 may be accessed through a small incision in each side of the neck. Clip position #4 may be reached only via an open chest. This clip would require the heart to be rolled sideways to get to the deep plexus.

FIG. 22 includes an electrical nerve stimulating device such as, for example, the electrical nerve stimulator disclosed in U.S. Pat. No. 5,458,625 of previous mention. The electrical signal is supplied to a control circuit 222 which includes a suitable switch means operable by a surgeon for supplying one or more preselected nerve stimulating signals to respective one or more clips and thus to desired vagus nerve positions.

In the course of momentarily stopping or slowing the heart during, for example, a coronary artery bypass graft procedure to facilitate the suturing procedure by the surgeon, it may be preferable to employ a heart pacing device such as illustrated in block diagram in FIG. 22. That is, a heart pacing device 224 may be attached in conventional fashion to the heart, to provide cooperating means for restarting the heart in accordance with the invention in the event that the heart is slow to revive after stimulus is removed from the vagus nerve.

The present invention is not limited to the scope of the foregoing detailed description, but is of the full scope of the claims appended hereto.

What is claimed:

1. A method of performing a selected surgical procedure on a patient's beating heart, comprising the steps of:
   momentarily arresting or substantially slowing the beating of the patient's heart using electrical stimulation; and
   performing at least one step of the selected surgical procedure while the patient's heart is momentarily arrested or substantially slowed.

2. The method of claim 1, wherein said momentarily arresting or substantially slowing using electrical stimulation comprises applying an electrical stimulating signal to a selected position on a vagus nerve of the patient to stimulate the vagus nerve to momentarily arrest or substantially slow the beating of the patient's heart.

3. The method of claim 1, further comprising the step of applying a heart pacing electrical signal to the patient's heart to restore the beating of the heart after cessation of said momentarily arresting or slowing, in the event that the heart is slow to revive after said cessation.

4. The method of claim 2, wherein said applying an electrical stimulating signal lasts for a period of about 10 seconds or less.

5. The method of claim 2, wherein said electrical stimulating signal is intermittently applied for periods of about 10 seconds or less, with predetermined rest periods between intermittent applications.

6. The method of claim 5, wherein said predetermined rest periods last for about thirty seconds each.

7. The method of claim 1, wherein said performing at least one step of the selected surgical procedure while the patient's heart is momentarily arrested or substantially slowed comprises performing at least one suturing step.

8. The method of claim 7, wherein the selected surgical procedure includes performing an anastomosis, and wherein said performing at least one suturing step comprises performing a series of suturing steps to complete the anastomosis, wherein at least one of said series of suturing steps is performed while the patient's heart is momentarily arrested or substantially slowed.

9. The method of claim 8, wherein said momentarily arresting or substantially slowing comprises applying an electrical stimulating signal to a selected position on a vagus nerve of the patient to simulate the vagus nerve to momentarily arrest or substantially slow the beating of the patient's heart.

10. The method of claim 9, wherein the vagus nerve is stimulated before each of the suturing steps in said series of suturing steps.

11. The method of claim 2, wherein said performing at least one step of the selected surgical precedure while the patient's heart is momentarily arrested or substantially slowed comprises forming an arteriotomy in a coronary artery to be bypassed.

12. A system for performing a selected surgical procedure on a beating heart, said system comprising:
    an electrical nerve stimulator for supplying a vagus nerve stimulating electrical signal from a location outside of a patient's body; and
    at least one electrical lead surrounded by insulative material with an electrode exposed from a distal end thereof, said electrode being adapted to be releasably fixed to the vagus nerve for supplying the vagus nerve stimulating electrical signal thereto.

13. The system of claim 12, wherein said electrode comprises an invasive needle or probe.

14. The system of claim 12, wherein said electrode comprises a non-invasive clip.

15. The system of claim 12, wherein said at least one said electrical lead with an electrode exposed comprises a plurality of said electrical leads, each of said electrodes adapted to contact the vagus nerve at different locations therealong.

16. The system of claim 15, wherein said plurality of electrical leads comprises a pair of electrical leads, each said electrical lead having one electrode exposed at an end thereof, wherein said electrodes are contacted with the vagus nerve in a bipolar arrangement.

17. The system of claim 16, wherein each said electrical lead comprises a clip with said electrode embedded therein.

18. The system of claim 12, wherein each of said at least one electrical leads comprises a clip having a pair of said electrode embedded therein, in opposition to one another.

19. The system of claim 18, wherein each said pair of electrodes has one electrode coupled to a positive potential of the electrical stimulator and the other electrode coupled to a negative potential.

20. The system of claim 12, further comprsing a heat pacing device connectable to the heart for reviving the heart, if needed, after cessation of the vagus nerve stimulating signal.

* * * * *